United States Patent [19]
Mark

[11] Patent Number: 5,451,791
[45] Date of Patent: Sep. 19, 1995

[54] WATER DISINFECTING APPARATUS

[76] Inventor: Farvell M. Mark, 4215 W. San Juan Ave., Phoenix, Ariz. 85019

[21] Appl. No.: 385,740

[22] Filed: Feb. 8, 1995

Related U.S. Application Data

[63] Continuation of Ser. No. 273,281, Jul. 11, 1994, abandoned, which is a continuation of Ser. No. 987,634, Dec. 9, 1992, abandoned.

[51] Int. Cl.$^6$ ............................ A61L 2/10; C02F 1/32
[52] U.S. Cl. ..................................... 250/438; 250/435
[58] Field of Search ................................ 250/435, 438

[56] References Cited

U.S. PATENT DOCUMENTS

| | | | |
|---|---|---|---|
| 2,738,427 | 3/1956 | Wagnon | 250/435 |
| 4,336,223 | 6/1982 | Hillman | 250/435 |
| 4,971,687 | 11/1990 | Anderson | 210/85 |

OTHER PUBLICATIONS

"Ultra-Hyd Germicidal Ultraviolet Water Purifiers".
"Pura Ultraviolet Plus".
"Ultra Sun".
"Ultra-Pure Water Through Ultra-Violet Treatment".
"What is Ultraviolet Light".
Censky, *Water Technology,* vol. 11, No. 8, Oct. 1988.
"Buyer's Market", pp. 1–2.

*Primary Examiner*—Jack I. Berman
*Attorney, Agent, or Firm*—Harry M. Weiss; Jeffrey D. Moy

[57] ABSTRACT

The output of a mechanical/chemical water filter(s) is conveyed through tubes transparent to ultraviolet radiation disposed in proximity to a source of ultraviolet radiation having the capability of disinfecting the water flowing through the tubes. Each of the opposed ends of the tubes is supported within a cylindrical cavity of a support member and retained in sealed engagement by a tube circumscribing O-ring clamped about the tube by a plate detachably attached to the support member. Passageways within the support member channel the water into or out of the respective tube end. The source of ultraviolet radiation is secured to opposed support members in close proximity to the tubes to enhance the bacteria, virus and micro organism killing capability of the ultraviolet radiation source.

3 Claims, 4 Drawing Sheets

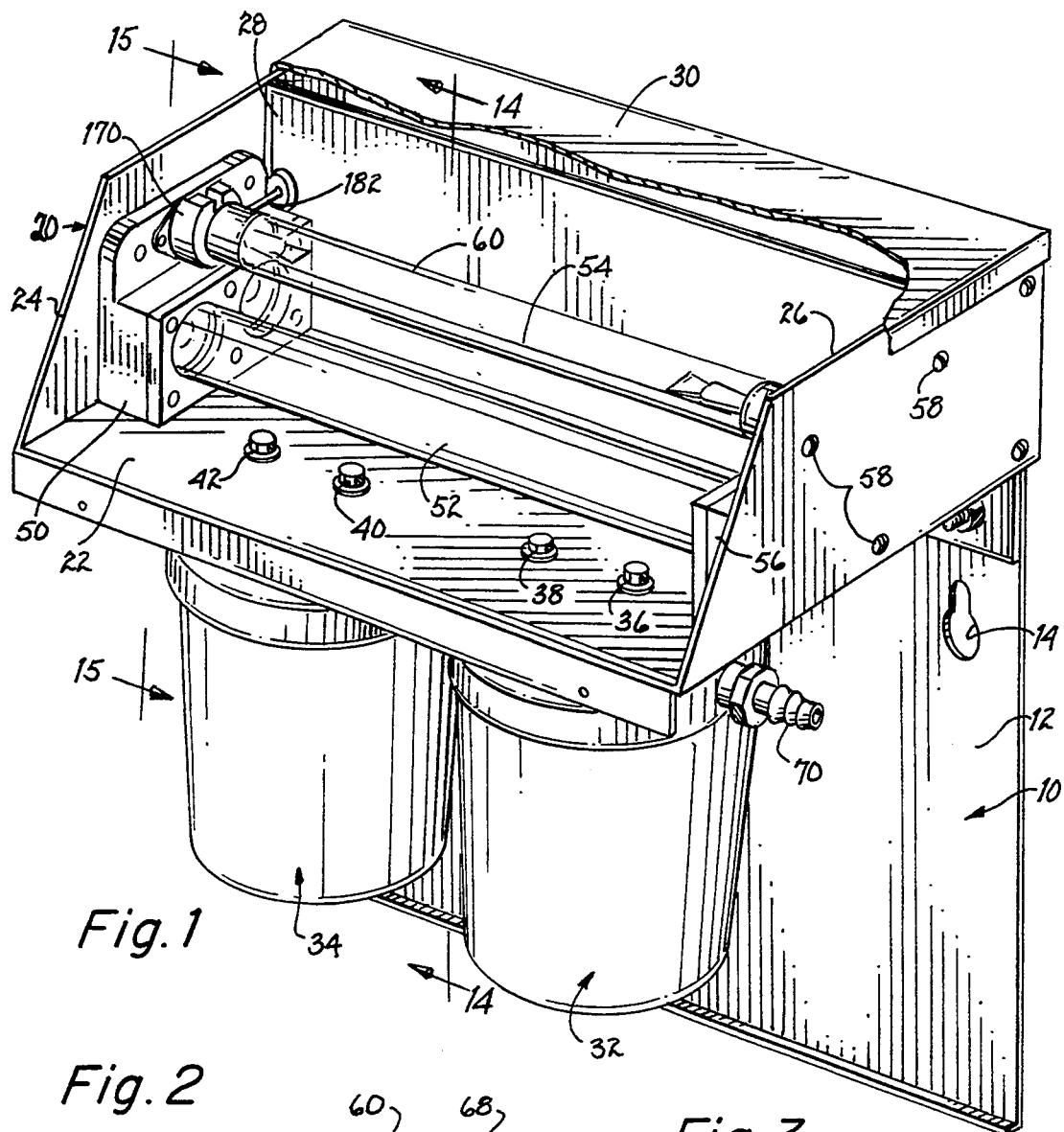
Fig. 1
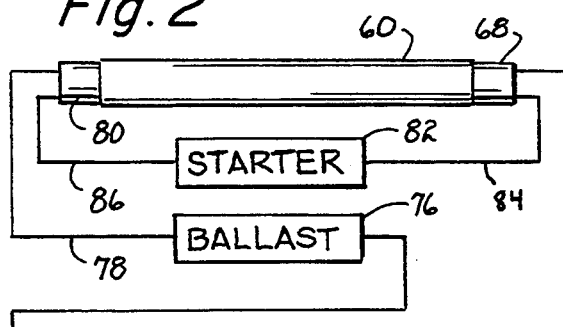
Fig. 2
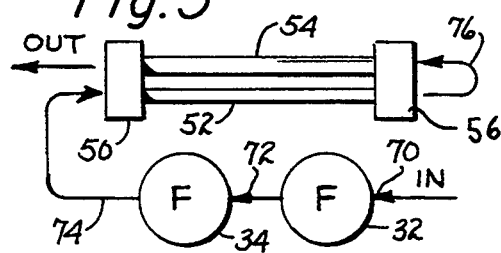
Fig. 3
Fig. 18

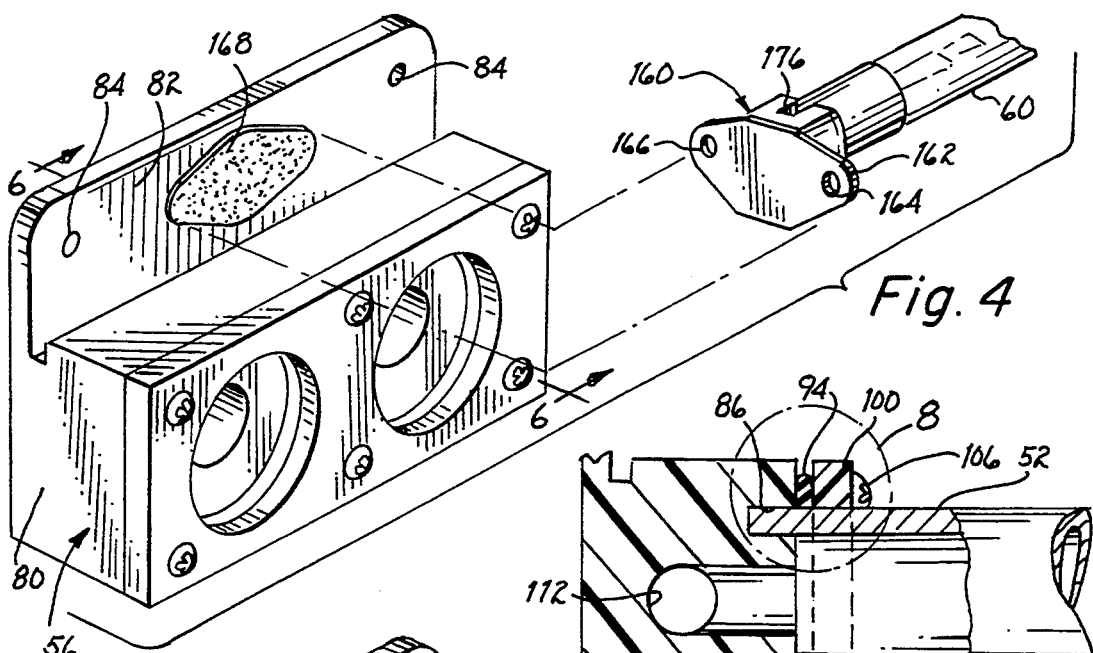
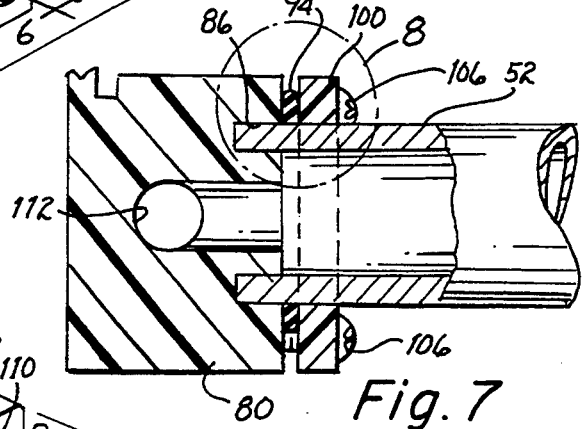
Fig. 4
Fig. 7
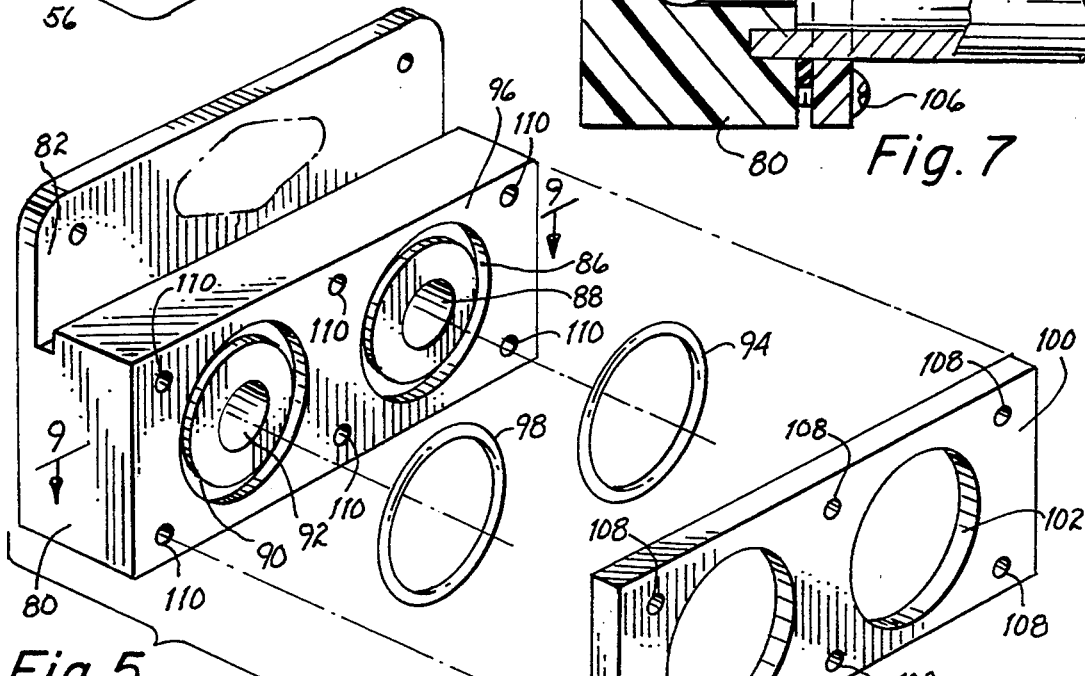
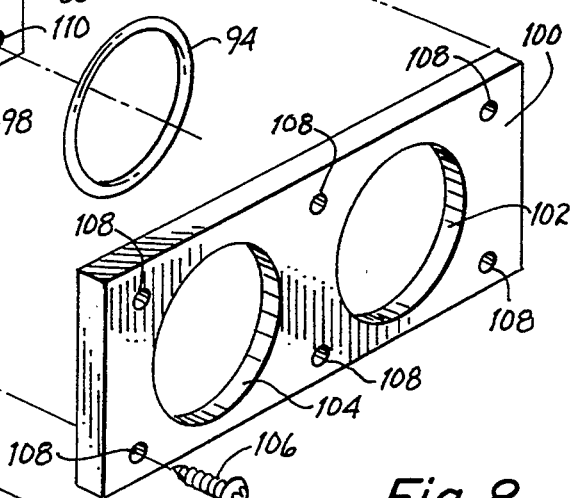
Fig. 5
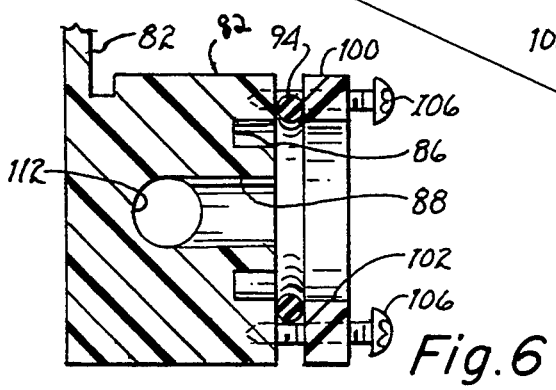
Fig. 6
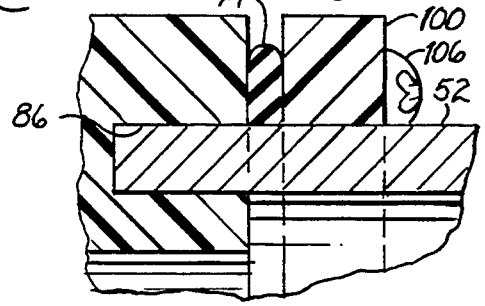
Fig. 8

WATER DISINFECTING APPARATUS

This is a continuation of application Ser. No. 08/273,281, now abandoned, filed on Jul. 11, 1994 which is a continuation of the patent application Ser. No. 07/987,634, now abandoned, filed on Dec. 9, 1992.

BACKGROUND OF THE INVENTION

1. Field of the Invention

The present invention relates to water disinfecting apparatus and, more particularly, to apparatus for supporting ultraviolet radiation transparent tubes proximate a source of ultraviolet radiation.

2. Description of Related Art

Mechanical and chemical filtration of water for drinking purposes is well known. Mechanical filtration filters sediment and particulate matter of a certain minimal size as a function of the filtration elements. Chemical filtration (such as activated charcoal) filters various chemicals that may be present. To kill bacteria, viruses and other microorganisms irradiation with radiant energy from a source of ultraviolet radiation is known. To achieve such kill results, the water is usually passed through a conduit transparent to ultraviolet radiation. The proximity of the source of ultraviolet radiation to such a conduit affects the intensity or concentration of the radiation dosage present. While many mechanisms exist for achieving a watertight junction between the ends of such conduits and a related tubing, such mechanisms are relatively bulky, require assembly by a skilled craftsman and have a multiple parts count. Furthermore, such mechanisms are not readily adaptable to accommodate a 90° change in flow path within a limited space.

At many locations for water disinfectant apparatus, space is at a premium and any available reduction of equipment size is desirable. Furthermore, the location of the source of ultraviolet radiation immediately proximate the ultraviolet radiation transparent conduits is preferably based on considerations of both use of space and increased effectiveness.

SUMMARY OF THE INVENTION

A mechanical water filter removes suspended and/or entrained particulate matter from water flowing therethrough as a function of the filtration capability of the filter elements. A chemical filter may be used to remove various chemicals. The viability of non filtered bacteria, viruses and micro organisms is destroyed by channeling the filtered outflow through ultraviolet transparent tubes located in close proximity with a source of ultraviolet radiation. Each of the tubes is supported within annular cavities disposed in opposed support members. A sealing engagement is effected through use of a tube circumscribing O-ring clamped in place at each support member by a tube penetrating plate. Each support member includes passageways for altering the direction into or out of the respective tube and in fluid communication with fittings secured to and extending from the respective support member. Such fittings are in fluid communication with the outflow of the mechanical/chemical filters or with a conduit discharging the filtered and irradiated water.

It is therefore a primary object of the present invention to provide a water disinfecting apparatus.

Another object of the present invention is to provide support members for supporting ultraviolet radiation transparent tubes of a water disinfecting apparatus.

Yet another object of the present invention is to provide support members for sealingly engaging fragile tubes while accommodating fluid flow into and out of such tubes.

Still another object of the present invention is to provide a low parts count support member for supporting a fragile tube while accommodating flow into and out of such tube along an axis not parallel with the longitudinal axis of the tube.

A further object of the present invention is to provide apparatus for sealingly supporting the end of a fragile tube in a support member having passageways in fluid communication with the tube.

A yet further object of the present invention is to provide apparatus for supporting a source of ultraviolet radiation in immediate proximity to water conveying ultraviolet radiation transparent tubes.

A still further object of the present invention is to provide a method for sealingly supporting ultraviolet radiation tubes in close proximity to a source of ultraviolet radiation.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is a perspective view of a water disinfecting apparatus with certain portions cutaway;

FIG. 2 is a simplified schematic of the circuit for energizing a source of ultraviolet radiation;

FIG. 3 depicts the water flow path of the apparatus illustrated in FIG. 1;

FIG. 4 is an exploded view of a support member for the tubes illustrated in FIG. 1;

FIG. 5 is an exploded view of the components of a support member illustrated in FIG. 4;

FIG. 6 is a cross sectional view taken along lines 6—6, as shown in FIG. 4;

FIG. 7 is a cross sectional view of a support member and attached tube;

FIG. 8 is a detail view taken within dashed line 8, as shown in FIG. 7;

FIG. 18 illustrates the water flow path through the variant illustrated in FIGS. 16 and 17.

DESCRIPTION OF THE PREFERRED EMBODIMENT

Figure 9:
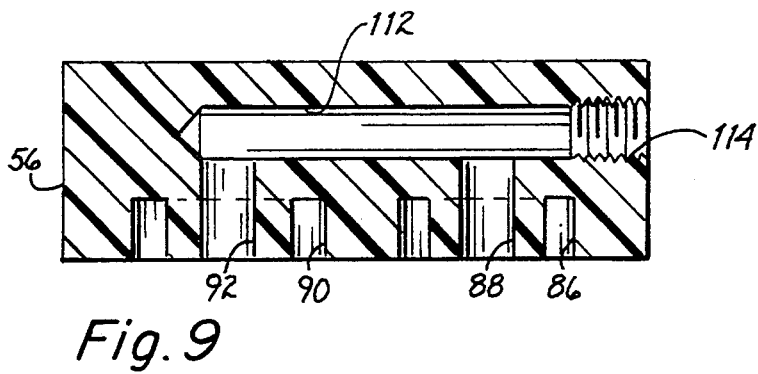
FIG. 9 is a cross sectional view taken along lines 9—9, as shown in FIG. 5.

Referring to FIG. 1, there is illustrated a water disinfectant apparatus 10. It includes a panel 12 for attachment to a wall or similar surface by means of hooks or other protrusions penetrably engaging keyholes of which keyhole 14 is illustrated. An enclosure 20 extends laterally from panel 12. The enclosure includes a base 22, sidewalls 24, 26 and a rear wall 28. A removable cover 30 extends across the top and the front of enclosure 10. A pair of filters 32 and 34, which filters may be mechanical, chemical or a combination, are supported by and depend from the under surface of base 22. Attachment means, such as bolts 36, 38 and 40, 42 may be used to secure filters 32, 34, respectively.

A support member 50 is attached to sidewall 24 and supports one end of a pair of tubes 52, 54. A further support member 56 supports the other end of the tubes. Fastening means 58 secure support member 56 to sidewall 26. Similar fastening means may be used to secure support member 50 to side wall 24. A source of ultraviolet radiation that may have a wavelength in the range of 2000 to 4000, Angstroms is provided by an elongated light 60 supported by and between support members 50 and 56. Tubes 52, 54 are of material transparent to the ultraviolet radiation emitted by light 60. Thus, any fluid, and any matter suspended or entrained therein, flowing through tubes 52, 54 will be subjected to ultraviolet radiation emitted from light 60. During normal operation, cover 30 contains the radiation emitted from light 60 within enclosure 20.

Referring to FIG. 2 there is illustrated a schematic wiring diagram for light 60. A light of this type is commercially available and is generally referred to as a germicidal UV lamp. Power is provided through a conventional power cord 62 that may be plugged via plug 64 into a conventional electrical outlet. Electrical conductor 66 is electrically connected to terminal 68 of light 60. Electrical conductor 70, including an inline fuse 72 and a switch 74, is electrically connected to a terminal of ballast 76. Electrical conductor 78 interconnects the other terminal of the ballast with terminal 80 of light 60. A starter 82 is electrically interconnected between terminal 68 and 80 via electrical conductors 84, 86. A thermistor 88 extends across electrical conductors 66 and 70. The operation of light 60 is conventional upon operation of switch 74. Furthermore, fuse 72 and thermistor 88 provide safety features in the event of misoperation of any of the components of the circuit.

Referring to FIG. 3, there is shown a schematic of the basic water flow through water disinfectant apparatus 10. Incoming water enters filter 32 via a nipple 70 (see FIG. 1). After an initial filtration, the water flows through a conduit 72 to filter 34. A conduit 74 conveys water from filter 34 to support member 50 and into tube 52. The outflow from this tube within support member 56 flows through a passageway 76 (represented by the depicted arrow) within support member 56 and into tube 54. The outflow from tube 54 flows through support member 50 and is discharged through a nipple. While the water flows through tubes 52 and 54, it is subjected to ultraviolet radiation from light 60. Such irradiation of the water will tend to kill any bacteria, viruses or any micro organisms in the water.

Support member 56 will be described with greater specificity with joint reference to FIGS. 4, 5, 6, 7 and 8. The support member includes a body 80 having an upwardly extending wall 82. This wall may include a plurality of apertures 84 for engagement by fastening means 58 (see FIG. 1). An annular groove 86 is formed in body 80 to receive an end of tube 52. A passageway 88 extends into body 80 from within the interior perimeter of the annular groove; the passageway may be concentric with the annular groove, as illustrated. A similar annular groove 90 is formed in body 80 to receive an end of tube 54. A passageway 92, disposed within the inner perimeter of the annular groove, extends into body 80. The purpose of passageway 88 is that of receiving an inflow of water from tube 52 while the purpose of passageway 92 is to discharge water into tube 54. The diameters of tubes 52 and 54 are substantially larger than those of passageways 88 and 92, as shown in the drawings, so as to cause the incoming water to decelerate as it reaches the area of the light. To prevent water leakage from within the tubes and through the respective annular grooves, an O-ring 94 is placed circumferentially about tube 52 adjacent face 96 of body 82. Similarly, an O-ring 98 is placed circumferentially about tube 54 adjacent face 96. To ensure a good seal between the circumferential surface of each of tubes 52 and 54 and face 96 of body 80, an apertured plate 100 is forced against face 96 to compress O-rings 94, 98 therebetween. The apertured plate includes apertures 102 and 104 for accommodating penetration of tubes 52 and 54. Fastening means, such as screws 106, penetrably engaging each of apertures 108, threadedly engage respective ones of cavities 110 in body 80. Upon tightening screws 106, the requisite pressure to squeeze the O-rings, as depicted in FIGS. 7 and 8, will occur. Such compression of the O-rings will force the O-rings into sealed engagement with the circumferential surface of the respective tubes and surface 96 of body 80. It may be noted that the apparatus for accommodating a seal about the end of each tube places very little stress upon the respective tube and the stress of an amount insufficient to endanger collapse or cracking of the tube.

In assembled form, support member 56 serves as passageway 76 depicted in FIG. 3 to provide a flow from the output of one tube to the input of the adjacent tube. This is accomplished by passageway 112 interconnecting passageways 92 and 88, as depicted in FIG. 9. If body 80 is made from a block of plastic, passageway 112 may be drilled to interconnect with drill holes forming passageways 88, 92. To prevent outflow of water from passageway 112 through the entry of the drill hole, the entry of the drill hole may be internally threaded with threads 114. A plug may then be threadedly mated to close the entry of the drill hole and prevent water outflow.

Figure 11:
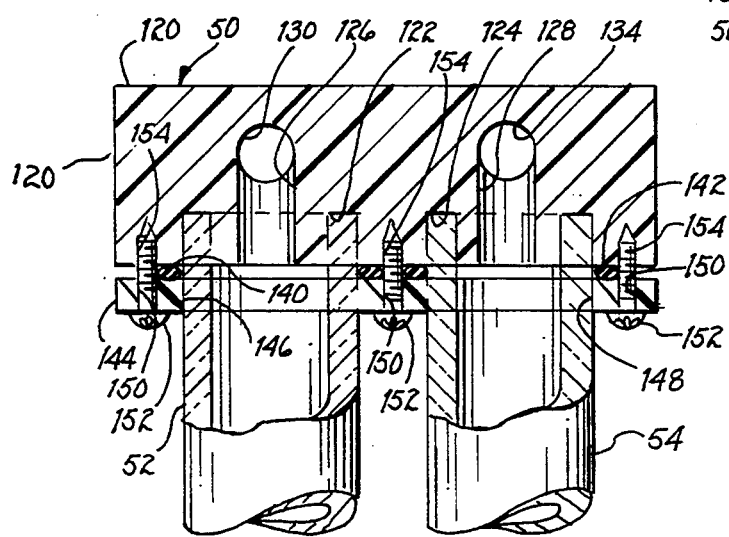
FIG. 11 is a cross sectional view taken along lines 11—11, as shown in FIG. 10.
Figure 12:
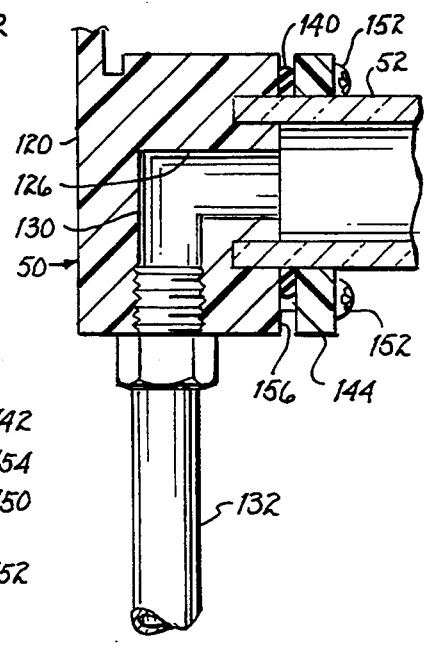
FIG. 12 is a partial cross sectional view taken along lines 12—12, as shown in FIG. 10.

Support member 50 will be described with joint reference to FIGS. 10, 11 and 12. Body 120 includes a pair of annular grooves 122, 124 for receiving and retaining respective ends of tubes 52, 54. Passageways 126, 128 extend interiorly into body 120 within the interior circumference of respective annular grooves 122, 124. These passageways may be concentric with the annular grooves, as illustrated. Passageway 126 serves the function of discharging fluid into tube 52 while passageway 128 serves the function of receiving fluid from tube 54. Passageway 126 includes a downwardly turned elbow 130 in threaded engagement with a nipple or conduit 132. Similarly, passageway 128 includes a downwardly extending elbow 134 in threaded engagement with a nipple or conduit 134. A pair of O-rings 140, 142 circumferentially extend about respective tubes 52, 54.

These O-rings serve the same sealing function discussed above with respect to O-rings 94, 98 associated with body 80 of support member 56. A plate 144 includes apertures 146, 148 for penetrably receiving the ends of tubes 52, 54 respectively. A plurality of holes 150 are disposed in plate 144 for penetrably receiving each of a plurality of fastening means, such as screws 152. Commensurate cavities 154 for threadedly receiving and engaging screws 152 are disposed within body 120. Upon penetrable engagement of the screws with holes 150 in plate 154 and threadedly engaging cavities 154, the plate becomes secured to body 120. Upon securing the plate, O-rings 140, 142, disposed about tubes 52, 54, are compressed, as illustrated. Such compression will cause the O-rings to form a tight seal against the outside cylindrical surface of the respective tubes and against face 156 of body 120 at the junction between the tubes and the face. The resulting seal will preclude leakage of fluid around the ends of the tubes and through annular grooves 122, 124.

Figure 10:
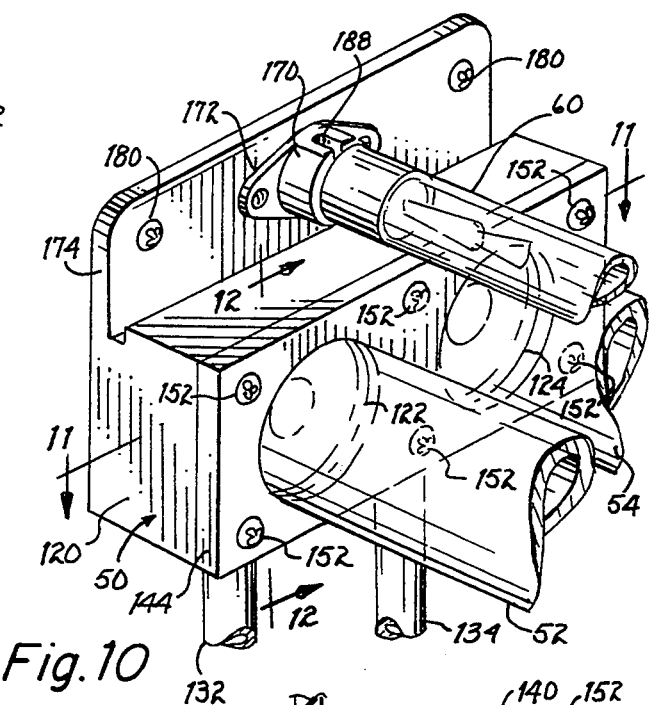
FIG. 10 is a perspective view illustrating a variant support member.

Referring jointly to FIGS. 1, 4 and 10, attachment of light 60 to support members 50, 56 will be described. Wall 82 extends upwardly from body 80 of support member 56 to serve a supporting function for socket 160. This socket includes a flange 162, which may have apertures 164, 166 for attachment to a supporting surface. Rather than using attachment means, such as nuts and bolts, rivets, machine screws of metal screws to secure flange 162 to wall 82, it has been found satisfactory to use double sided sticky tape to perform the attaching function. Such sticky tape is very inexpensive and requires minimal labor for installation. Furthermore, the strength provided is sufficient to meet all expected loads placed thereon by light 60, including installation and removal of the light. Socket 170 is also secured by double sided sticky tape 172 to wall 184 extending upwardly from body 120 of support member 50. Socket 170 is, for all intents and purposes, a duplicate of socket 160. Sockets 160, 170, being of conventional configuration and readily available in the marketplace, include entry slots 176, 188 to accommodate the prongs of light 60, upon installation and removal of the light. As is conventional, after downward insertion of the prongs of the light into the respective slots, the light is rotated approximately 90° to establish electrical contact between the light prongs and corresponding electrical contacts within sockets 160, 170.

As noted in FIG. 10, wall 174 includes apertures for penetrably receiving screws 180 to secure the wall and support member 50 to sidewall 24 of enclosure 20 (see FIG. 1). As also shown in FIG. 1, an electrical conductor 182 extends from socket 170 to provide electrical power to light 60, as reflected in the schematic illustrated in FIG. 2. A similar conductor is associated with socket 160.

Figure 13:
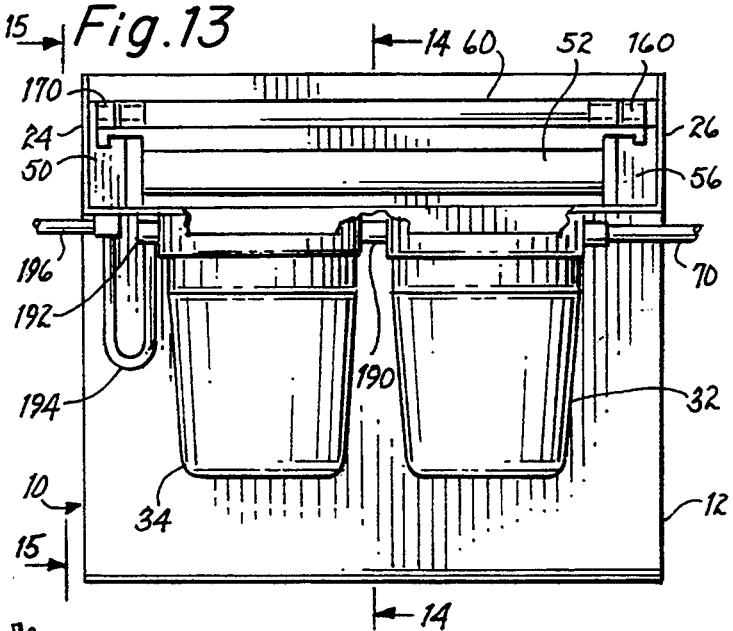
FIG. 13 is a front view of the apparatus shown in FIG. 1.
Figure 14:
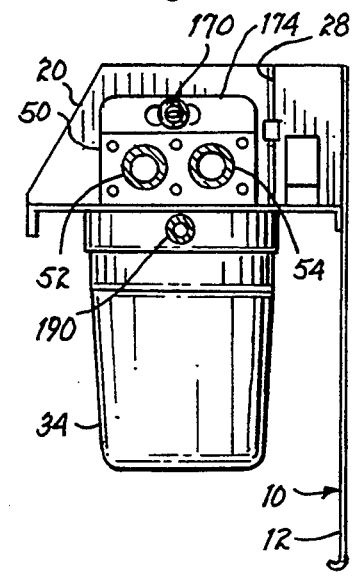
FIG. 14 is a partial cross sectional view taken along lines 14—14, as shown in FIG. 13.
Figure 15:
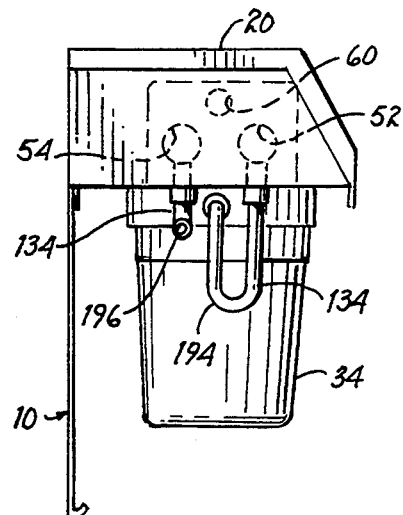
FIG. 15 is a side view taken along lines 15—15, as shown in FIG. 13.

Referring jointly to FIGS. 13, 14 and 15, further details attendant the assembly of water disinfectant apparatus 10 will be described. For purposes of illustration, FIGS. 13 and 14 illustrate enclosure 20 with cover 30 removed. Water to be filtered and purified enters filter 32 through nipple 70. The filtered water is conveyed via conduit 190 to the input to filter 34. The second stage filtered water is discharged from filter 34 through outlet 192. Tubing 194 extends from this outlet and interconnects with or becomes conduit 132 (see FIG. 12) extending from support member 50. The filtered water flows through conduit 132 into elbow 130 and passageway 126 of body 120 into tube 52. As the water passes through tube 52, it is subjected to the virus, bacteria micro organism killing properties of ultraviolet radiation emitted by light 60. The water discharged from tube 52 flows into support member 56 through passageway 88, passageway 112 and passageway 92 (see FIGS. 5 and 7) and into tube 54. The water returning to support member 50 through tube 54 is again subjected to ultraviolet radiation from light 60. The water discharged from tube 54 flows through passageway 128 and elbow 134 and is discharged through conduit 134. This conduit may include an elbow to provide for connection with horizontal tubing 196. The filtered and disinfected water discharged from tubing 196 is now ready for use. The above described water flow is schematically illustrated in FIG. 3, as described earlier.

Figure 16:
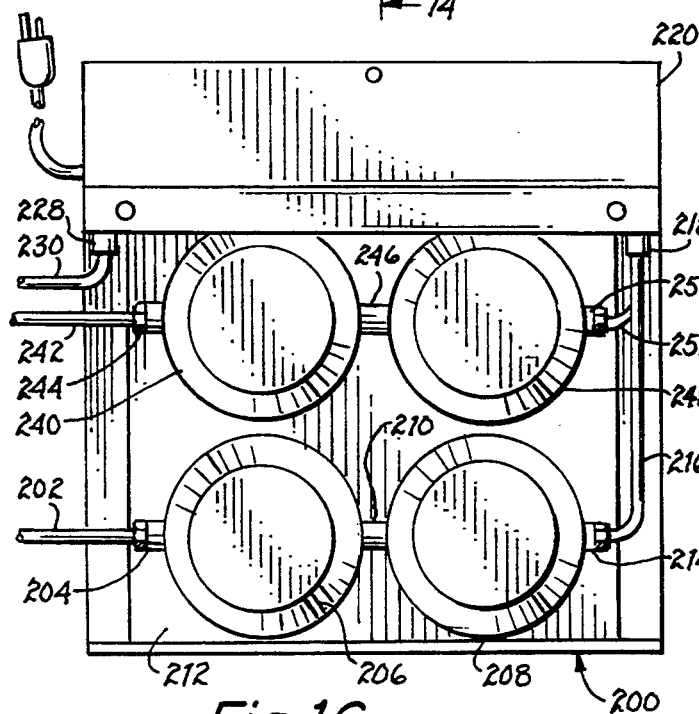
FIG. 16 is a front view illustrating a variant of the apparatus shown in FIG. 1.
Figure 17:
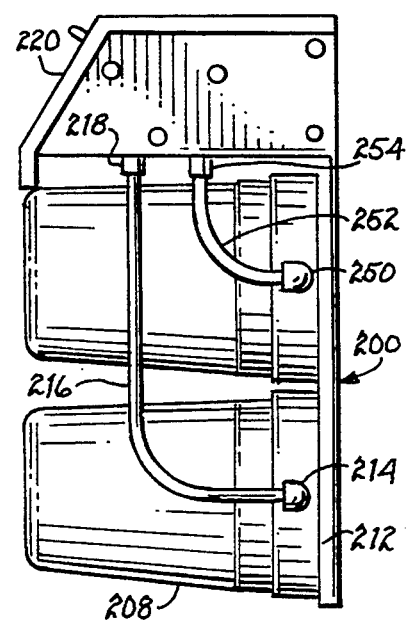
FIG. 17 is a side view of the variant illustrated in FIG. 16.

Referring jointly to FIG. 16, 17 and 18 there will be described a variant of the water disinfecting apparatus for accommodating different water flows of hot and cold water. Variant 200 includes a conduit 202 for receiving cold water from a source of cold water. The conduit is mechanically connected to a nipple 204 attached to a filter 206. Outflow from the filter is conveyed to a further filter 208 via an interconnecting conduit 210. Both of these filters are mounted upon panel 212. The outflow from filter 208 occurs through nipple 214 interconnected with a conduit 216. The conduit conveys the filtered cold water to a conduit or nipple 218 extending downwardly from within enclosure 220 of variant 200. Enclosure 220 includes components comparable with these described above with regard to water disinfecting unit 10. A support member 222 (see FIG. 18), duplicative of support member 50, receives the filtered water through nipple 218 and discharges the water into a tube 224 disposed within enclosure 220, which tube is transmissive to ultraviolet radiation emitted from a light disposed within the enclosure. The outflow from tube 224 is through support member 226 (which is also duplicative of support member 50), through a nipple 228 and into a conduit 230. The outflow from conduit 230 is water that has been mechanically/chemically filtered of suspended and entrained particulate matter and undesired chemicals and disinfected to kill bacteria, viruses and micro organisms responsive to the ultraviolet radiation emitted by an ultraviolet radiating source (such as light 60) within enclosure 220.

Hot water, from a source of hot water, flows into filter 240 via conduit 242 and nipple 244. The filtered water is discharged through conduit 246 into a further filter 248. The outflow from filter 248 flows through a nipple 250 into conduit 252 and through a further nipple 254 into support member 222. Filters 240 and 248 may be mechanical and/or chemical filters. Support member 222 channels the inflowing hot water into a tube 254, which tube is transmissive to ultraviolet radiation from the light within enclosure 220. Outflow of water from tube 254 is conveyed through support member 226 through a further nipple and into a conduit 258. Accordingly, hot water which has been mechanically/chemically filtered and disinfected by killing of germs, bacteria and micro organisms responsive to ultraviolet radiation is available at the output of conduit 258.

From the above description of variant 200 it will become apparent that the fundamental structure of water disinfectant apparatus 10 may be adapted to mechanically/chemically filter and disinfect water, or any fluid, flowing in through a single conduit and discharging through a single conduit or, the basic apparatus may be employed to simultaneously filter and disinfect each of two independent streams of fluid inflowing through two conduits and discharged through two corresponding conduits. The main difference between water disinfecting apparatus 10 and variant 200 is that of employing two support members of the type identified by the numeral 50 instead of a support member of the type identified by numeral 50 and a further support member identified by the numeral 56 to provide a return path past the ultraviolet radiation emitting light. The differences associated with the mounting of the mechanical filters is primarily a matter of engineering preferences and minimizing complexity and space requirements. That is, enclosure 220 could be constructed to include a base (22) of sufficient size to support two sets of two mechanical filters. Alternatively, a single filter could be used to filter the water of each incoming water conduit (see variant 200) by simply rearranging the plumbing.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. Apparatus for filtering and disinfecting a fluid flowing from a source of fluid to a discharge conduit, said apparatus comprising in combination:
   a) filter means for filtering the fluid;
   b) a source of ultraviolet light radiation for irradiating the fluid filtered by said filter means;
   c) a tube for conveying the fluid past said source of ultraviolet radiation to irradiate the conveyed fluid, said tube having an inlet and an outlet;
   d) a first support member for supporting said inlet, said first support member including a cavity for receiving said inlet to establish a junction between said inlet and said first support member, means circumscribing and adjacent to said inlet for sealing said junction and means for compressing said circumscribing means to form a seal at said junction and to prevent leakage of fluid between said first support member and said inlet, said compressing means having a substantially flat surface portion situated parallel to a flat portion of said first support member for forming said seal evenly;
   e) a second support member for supporting said outlet, said second support member including a further cavity for receiving said outlet to establish a further junction between said outlet and said second support member, further means circumscribing and adjacent to said outlet for sealing said further junction and further means for compressing said further circumscribing means to form a further seal at said further junction and to prevent leakage of fluid between said second support member and said outlet, said further compressing means having a substantially flat surface portion situated parallel to a flat portion of said second support member for forming said further seal evenly;
   f) means for conveying the fluid from said filter means to said inlet through said support member;
   g) further means for conveying the irradiated fluid to the discharge conduit;
   h) each of said first and second support members includes means for mounting said source of ultraviolet radiation therebetween and above said tube, said source of ultraviolet radiation comprises a tubular light and wherein said mounting means comprises a pair of opposed sockets for receiving said tubular light, and wherein double sided sticky tape is included for securing each socket of said pair of sockets to the respective one of said first and second support members;
   i) a further tube for conveying the fluid past said source of ultraviolet radiation to irradiate the conveyed fluid, said further tube having a further inlet and a further outlet,
   j) said second support member including means for supporting said further inlet comprising a yet further cavity for receiving said further inlet to establish a yet further junction between said further inlet and said second support member, yet further means circumscribing and adjacent to said further inlet for sealing said yet further junction and yet further means for compressing said yet further circumscribing means to form a seal at said yet further junction and to prevent leakage of fluid between said second support member and said further inlet, said yet further compressing means having a substantially flat surface portion situated parallel to a flat portion of said second support member for forming said seal evenly;
   k) means for establishing fluid communication between said outlet and said further inlet;
   l) said first support member including means for supporting said further outlet comprising a still further cavity for receiving said further outlet to establish a still further junction between said further outlet and said first support member, still further means circumscribing and adjacent to said further outlet for sealing said still further junction and still further means for compressing said yet further circumscribing means to form a seal at said still further junction and to prevent leakage of fluid between said first support member and said further outlet, said still further compressing means having a substantially flat surface portion situated parallel to a flat portion of said first support member for forming said seal evenly;
   m) diameters of said tube and said further tube being substantially larger than a diameter of each of said means for conveying the fluid from said filter means to said inlet through said support member, means for establishing fluid communication between said outlet and said further inlet, and further means for conveying the irradiated fluid to the discharge conduit; and
   n) a removable cover located above said source of ultraviolet light radiation, said tube and said further tube.

2. The apparatus as set forth in claim 1 wherein each of said circumscribing means, said further circumscribing means, said yet further circumscribing means and said still further circumscribing means comprises an O-ring, and wherein said compressing means and said still further compressing means comprises a first apertured plate for penetrably receiving said inlet and said further outlet, and means for securing said first apertured plate to said first support member and said further compressing means and said yet further compressing means comprises a second apertured plate for penetrably receiving said outlet and said further inlet and further means for securing said second apertured plate to said second support member.

3. The apparatus as set forth in claim 2 wherein each of said first and second support members includes means for mounting said source of ultraviolet radiation therebetween and equidistant and above said tube and said further tube, and wherein said source of ultraviolet radiation comprises a tubular light and wherein said mounting means comprises a pair of opposed sockets for receiving said light.

* * * * *